(12) United States Patent
Olberg et al.

(10) Patent No.: US 8,530,620 B2
(45) Date of Patent: Sep. 10, 2013

(54) RADIOLABELLING REAGENTS AND METHODS

(75) Inventors: Dag Erlend Olberg, Oslo (NO); Joseph Maduabuchi Arukwe, Oslo (NO)

(73) Assignee: GE Healthcare Limited, Buckinghamshire (GB)

(*) Notice: Subject to any disclaimer, the term of this patent is extended or adjusted under 35 U.S.C. 154(b) by 18 days.

(21) Appl. No.: 13/256,511

(22) PCT Filed: Mar. 22, 2010

(86) PCT No.: PCT/US2010/028078
§ 371 (c)(1),
(2), (4) Date: Sep. 14, 2011

(87) PCT Pub. No.: WO2010/114723
PCT Pub. Date: Oct. 7, 2010

(65) Prior Publication Data
US 2012/0022227 A1 Jan. 26, 2012

Related U.S. Application Data

(60) Provisional application No. 61/164,494, filed on Mar. 30, 2009.

(30) Foreign Application Priority Data

Mar. 30, 2009 (GB) .................... 0905438.8

(51) Int. Cl.
*C07K 5/00* (2006.01)
*C07K 7/00* (2006.01)

(52) U.S. Cl.
USPC ........... 530/303; 530/328; 530/331; 530/399; 530/409

(58) Field of Classification Search
USPC ......... 530/303, 328, 331, 399, 409; 546/322, 546/310
See application file for complete search history.

(56) References Cited

FOREIGN PATENT DOCUMENTS

| FR | 2926079 | | 7/2009 |
|---|---|---|---|
| WO | 2004/002984 | | 1/2004 |
| WO | WO 2004002984 | * | 1/2004 |
| WO | 2004/080492 | | 9/2004 |
| WO | 2005/012335 | | 2/2005 |

OTHER PUBLICATIONS

C-Y Shiue: "Synthesis of 18F-Labelled N-(P-[18F] Fluorophenyl)Maleimide and Its Derivatives for Labelling Monoclonal Antibody With 18F" Journal of Labelled Compounds and Radiopharmaceuticals, John Wiley, Chichester, GB. vol. 26, Jan. 1, 1989 pp. 287-289.
Olberg D E et al: "One Step Radiosynthesis of 6-[18F] Fluoronicotinic Acid 2, 3, 5, 6-Tetrafluorophenyl Ester ([F]F-PY-TFP). A New Prosthetic Group for Efficient Labelling Biomolecules with Fluorine-18". Journal of Medicinal Chemistry, vol. 53, Jan. 20, 2010 pp. 1732-1740.
PCT/US2010/028078 ISRWO May 25, 2010.
GB0905438.8 Search Report Jun. 18, 2009.

* cited by examiner

*Primary Examiner* — Michael G Hartley
*Assistant Examiner* — Jagadishwar Samala

(57) ABSTRACT

The present invention relates to reagents and methods for [$^{18}$F]-fluorination of biomolecules, particularly of peptides. The resultant $^{18}$F-labelled compounds are useful as radiopharmaceuticals, specifically for use in Positron Emission Tomography (PET).

8 Claims, No Drawings

RADIOLABELLING REAGENTS AND METHODS

This application is a filing under 35 U.S.C. 371 of international application number PCT/US2010/028078, filed Mar. 22, 2010, which claims priority to U.S. application Ser. No. 61/164,494 filed Mar. 30, 2009 and Great Britain application number 0905438.8 filed Mar. 30, 2009, the entire disclosure of which is hereby incorporated by reference.

The present invention relates to reagents and methods for [$^{18}$F]-fluorination of biomolecules, particularly of peptides. The resultant $^{18}$F-labelled compounds are useful as radiopharmaceuticals, specifically for use in Positron Emission Tomography (PET).

The application of radiolabelled bioactive peptides for diagnostic imaging is gaining importance in nuclear medicine. Biologically active molecules which selectively interact with specific cell types are useful for the delivery of radioactivity to target tissues. For example, radiolabelled peptides have significant potential for the delivery of radionuclides to tumours, infarcts, and infected tissues for diagnostic imaging and radiotherapy. $^{18}$F, with its half-life of 110 minutes, is the positron-emitting nuclide of choice for many receptor imaging studies. Therefore, $^{18}$F-labelled bioactive peptides have great clinical potential because of their utility in PET to quantitatively detect and characterise a wide variety of diseases.

One difficulty with preparing $^{18}$F-labelled peptides is that the existing $^{18}$F-labelling reagents are time-consuming to prepare. Efficient labelling of peptides and proteins with $^{18}$F is only achieved by using suitable prosthetic groups. Several such prosthetic groups have been proposed in the literature, including N-succinimidyl-4-[$^{18}$F]fluorobenzoate, m-maleimido-N-(p-[$^{18}$F]fluorobenzyl)-benzamide, N-(p-[$^{18}$F]fluorophenyl)maleimide, and 4-[$^{18}$F]fluorophenacylbromide. Almost all of the methodologies currently used today for the labelling of peptides and proteins with $^{18}$F utilise active esters. The most commonly used $^{18}$F-labelling reagent is N-succinimidyl-4-[$^{18}$F]fluorobenzoate (SFB). SFB suffers from the disadvantage that it takes 3 synthetic steps to prepare (fluorination, hydrolysis, and generation of active ester), followed by a time-consuming HPLC purification step—thus the preparation of SFB is difficult to automate. Furthermore, the presence of the phenyl ring in the labelling reagent adds significant hydrophobicity to the $^{18}$F-labelled product which can adversely affect its biodistribution profile. Therefore, there still exists a need for alternative $^{18}$F-labelling reagents and methodologies which allow rapid, chemoselective introduction of $^{18}$F, particularly into peptides, under mild conditions to give $^{18}$F-labelled products. Additionally, there is a need for such methodologies which are amenable to automation to facilitate preparation of radiopharmaceuticals in the clinical setting.

According to a first aspect of the invention, there is provided a compound of formula (I):

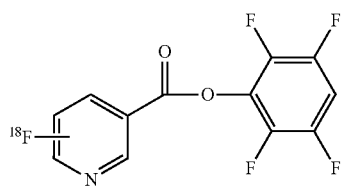

(I)

In one aspect, the $^{18}$F label is attached ortho—to the pyridyl nitrogen such that the compound of formula (I) has formula (Ia):

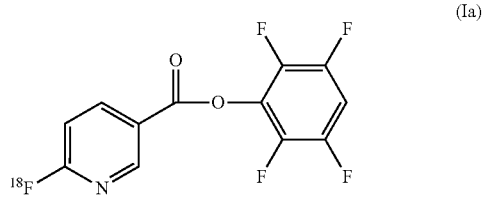 [SMILES: O=C(Oc1c(F)c(F)cc(F)c1F)c1ccc([18F])nc1]

(Ia)

The compounds of formula (I) and (Ia) should add significant advantages for the $^{18}$F-labelling of biomolecules. The compounds of formula (I) and (Ia) can be $^{18}$F-labelled in one step, the labelling is fast at near room temperature, purification can be done with a cartridge based system (for example, Oasis MCX column) which render automation more amendable. Also the pyridine system is known to be more hydrophilic than the benzyl analogue and is therefore expected to add a positive impact on the biodistribution profile of the $^{18}$F-product. As demonstrated below, the tetrafluoro phenyl ester has been found to be more stable during $^{18}$F-labelling than other active esters Compounds of formula (I) and (Ia) may be prepared from the corresponding compound of formula (II):

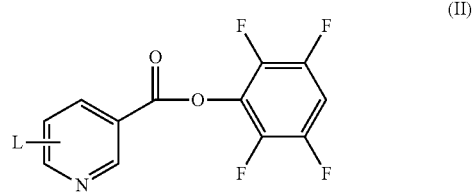

(II)

or a salt thereof, wherein L is a leaving group selected from chloro, bromo, iodo, nitro, and tri($C_{1-6}$alkyl)ammonium (suitably trimethyl ammonium). Such compounds of formula (II) are novel and therefore form a further aspect of the invention.

In one aspect, L in the compound of formula (II) is tri($C_{1-6}$alkyl)ammonium (suitably trimethyl ammonium), with a suitable counterion selected from those derived from mineral acids, for example hydrochloric, hydrobromic, phosphoric, metaphosphoric, perchloric acid, nitric, and sulphuric acids, and those derived from organic acids, for example tartaric, trifluoroacetic, citric, malic, lactic, fumaric, benzoic, glycollic, gluconic, succinic, methanesulphonic, trifluoromethanesulphonic, and para-toluenesulphonic acids; suitably selected from chloride, bromide, perchlorate, sulphonate, nitrate, phosphate, and trifluoromethanesulphonate, more suitably with a trifluoromethanesulphonate counterion.

In one aspect, the compound of formula (II) is:

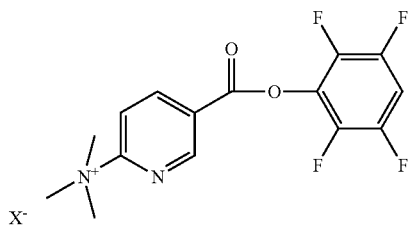

wherein X$^-$ is a counterion as defined above, and is preferably trifluoromethanesulphonate.

Preparation of a Compound of Formula (I) from the Corresponding Compound of Formula (II) or Salt thereof may be effected by standard $^{18}$F-labelling methods. [$^{18}$F]fluoride is conveniently prepared from $^{18}$O-enriched water using the (p,n)-nuclear reaction, (Guillaume et al, Appl. Radiat. Isot. 42 (1991) 749-762) and generally isolated as a salt such as Na$^{18}$F, K$^{18}$F, Cs$^{18}$F, tetraalkylammonium [$^{18}$F]fluoride, or tetraalkylphosphonium $^{18}$F fluoride. To increase the reactivity of the [$^{18}$F]fluoride, a phase transfer catalyst such as an aminopolyether or crown ether, for example, 4,7,13,16,21,24 hexaoxa-1,10-diazabicyclo[8,8,8]hexacosane (Kryptofix 2.2.2) may be added and the reaction performed in a suitable solvent. These conditions give reactive fluoride ions. Optionally, a free radical trap may be used to improve fluoridation yields, as described in WO 2005/061415. The term "free radical trap" is defined as any agent that interacts with free radicals and inactivates them. A suitable free radical trap for this purpose may be selected from 2,2,6,6-Tetramethylpiperidine-N-Oxide (TEMPO), 1,2-diphenylethylene (DPE), ascorbate, para-amino benzoic acid (PABA), α-tocopherol, hydroquinone, di-t-butyl phenol, β-carotene and gentisic acid.

The treatment of a compound of formula (II) with [$^{18}$F] fluoride may be effected in the presence of a suitable organic solvent such as acetonitrile, dimethylformamide, dimethylsulphoxide, dimethylacetamide, tetrahydrofuran, dioxan, 1,2 dimethoxyethane, sulpholane, N-methylpyrrolidininone, or in an ionic liquid such as an imidazolium derivative (for example 1-ethyl-3-methylimidazolium hexafluorophosphate), a pyridinium derivative (for example, 1-butyl-4-methylpyridinium tetrafluoroborate), a phosphonium compound, or tetralkylammonium compound at a non-extreme temperature, for example, 15° C. to 50° C., preferably at around ambient temperature such as 15° C. to 30° C., for example 18° C. to 25° C.

Compounds of formula (II) and salts thereof may be prepared from commercially available starting materials such as 6-chloro-nicotinc acid. Yields for the overall process are good (>50%). The steps included esterification with tetrafluorophenol activated for example by dicyclohexyl carbodiimide (DCC), generation of the trimethylammonium salt by treating the active 6-chloro nicotinic acid-ester with a saturated solution of trimethylamine in tetrahydrofuran (THF), and generation of the trifluoromethanesulphonate (triflate) salt with silver triflate.

Following preparation of a compound of formula (I), it may be purified by standard methods, typically using solid phase extraction for example with an Oasis MCX™ column, from which the compound of formula (I) can be eluted with good purity using a suitable organic solvent/water mixture.

According to a further aspect of the invention, there is provided a method for $^{18}$F-fluorination comprising reaction of a compound of formula (I) with a compound of formula (III):

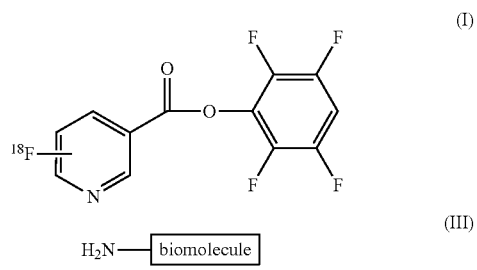

to give an $^{18}$F-product of formula (IV):

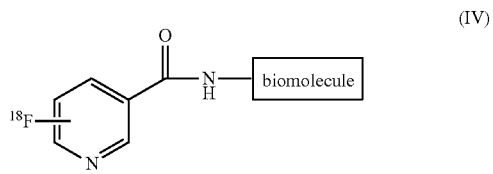

The reaction of a compound of formula (I) with a compound of formula (III) may be effected in a suitable solvent, for example, in an aqueous buffer in the pH range 2 to 11, suitably 3 to 11, and at a non-extreme temperature of from 5 to 70° C., preferably at ambient temperature.

In formulae (III) and (IV) suitable biomolecules for labelling are peptides, which may include somatostatin analogues, such as octreotide, bombesin, vasoactive intestinal peptide, chemotactic peptide analogues, α-melanocyte stimulating hormone, neurotensin, Arg-Gly-Asp peptide and its analogues, human pro-insulin connecting peptide, endothelin, angiotensin and formyl-norleucyl-leucyl-phenylalanyl-norleucyl-tyrosyl-lysine. Preferred peptides for labelling are Arg-Gly-Asp peptide and its analogues, such as those described in WO 01/77415 and WO 03/006491. Preferred peptides comprise the fragment:

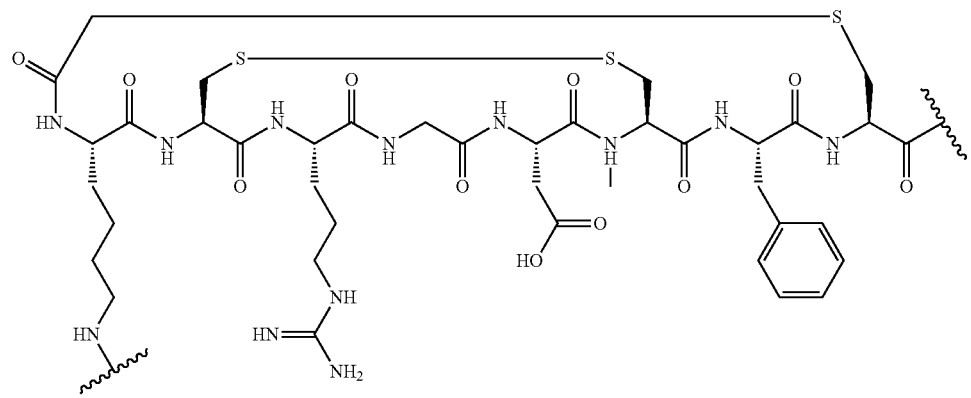 [SMILES: *NCCCC[C@@H]1NC(=O)CSC[C@@H](C(*)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2C]

In one particular aspect, the biomolecule in formula (III) or (IV) is a peptide of formula (A):

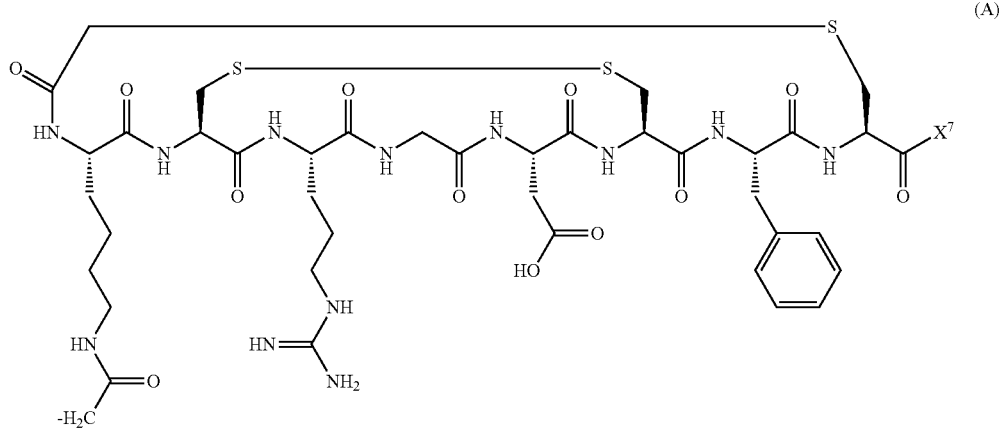

wherein $X^7$ is either —$NH_2$ or

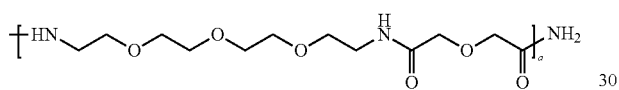

wherein a is an integer of from 1 to 10, preferably a is 1.

As will be appreciated by the skilled person, the methods of the invention may also be used for $^{18}$F-fluorination of other biomolecules such as proteins, hormones, oligonucleotides, and antibody fragments, as well as small drug-like molecules to provide a variety of PET tracers.

Compounds of formula (III) may be prepared by standard methods of peptide synthesis, for example, solid-phase peptide synthesis, for example, as described in Atherton, E. and Sheppard, R. C.; "Solid Phase Synthesis"; IRL Press: Oxford, 1989. Incorporation of the primary amine group in a compound of formula (III) may be achieved by reaction of the N or C-terminus of the peptide or with some other functional group contained within the peptide sequence, modification of which does not affect the binding characteristics of the vector. The primary amine group is preferably introduced by formation of a stable amide bond formed by reaction of a peptide amine function with an activated acid and introduced either during or following the peptide synthesis. When the precursor is an acid then the primary amine can be introduced using in situ activating agents such as 2-(1H-benzotriazole-1-yl)-1,1, 3,3-tetramethyluronium hexafluorophosphate (HBTU) or N-[(dimethylamino)-1H-1,2,3-triazolo[4,5-b]pyridin-1-yl-methylene]-N-methylmethanaminium hexafluorophosphate N-oxide (HATU).

The invention will now be illustrated by way of example only.

EXAMPLES

Example 1

Synthesis of 6-Fluoro-nicotinic acid 2,3,5,6-tetrafluoro-phenyl ester

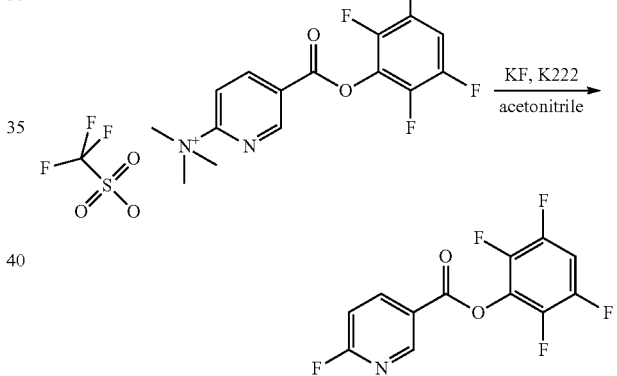

2,3,5,6-tetrafluorophenol (Tfp) active ester of 2-trimethylammonium nicotinic acid was synthesised in three steps starting from 6-chloro nicotinic acid (Sigma-Aldrich). Esterification of 6-chloro nicotinic acid (3 g, 19 mmol) with 2,3,5, 6-tetrafluorophenol (3.25 mg, 19 mmol)) activated by dicyclohexyl carbodiimide (DCC) (3.96, 19 mmol) in 50 mL dioxane following crystallization from hexane gave the 6-chloro nicotinc acid Tfp ester in 73% yield. Generation of the trimethylammonium salt by treating the active 6-chloro nicotinic acid tfp-ester (1 g, 3.27 mmol) in a saturated solution of trimethylamine (continuous bubbling for two hours) in tetrahydrofuran (THF) (15 mL), gave the trimethylammonium salt with chloride as counterion in 45% yield. Unreacted material could be filtered away since the salt precipitates out of the tetrahydrofuran solution. Generation of the triflate salt can be achieved in two ways; either treatment of the corresponding chloride salt with silver triflate in 1.2 molar excess in acetonitrile or treatment with trimethylsilyl trifluoromethanesulfonate. The latter is the preferred choice as work-up is simpler and no preparative chromatography is needed. Both methods are almost quantitative.

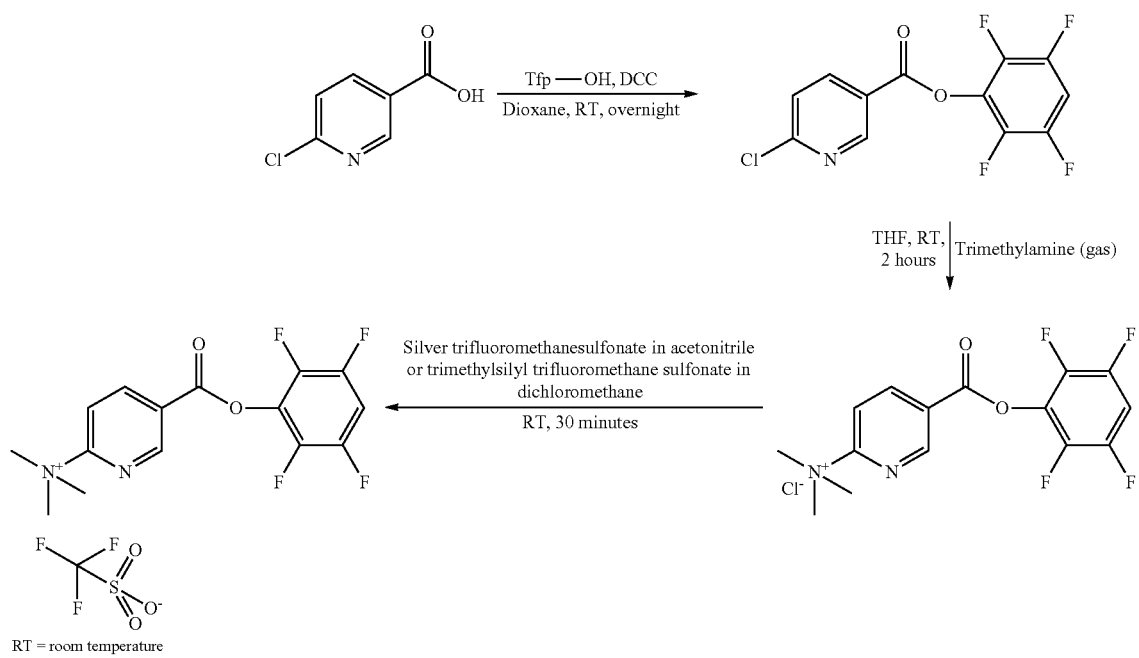

RT = room temperature

The synthesized precursor (9.2 mg) was initially labelled with $^{19}F$ by means of K222 (10 mg) and KF (1.1 mg) in acetonitrile (0.7 ml). The reaction of $^{19}F$ with the Tfp ester was studied using 1H-NMR in acetonitrile-d6 at 27° C. to assay reaction kinetics and impurities formed.

Comparative Example

The N-hydroxysuccinimide (NHS) ester of 2-trimethylammonium nicotinic acid was synthesised from 6-chloro nicotinic acid and labelled with $^{19}F$ by analogy to the methods above.
Results:

Both esters were synthesized in good yields (>30% starting from 6-chloro nicotinic acid) and reacted readily with fluoride in acetonitrile at room temperature. The NHS-ester was more prone to hydrolysis than the Tpf-ester and was thus not evaluated further. Studies of the reaction Tfp-ester by 1H-NMR over 30 minutes showed rapid incorporation of fluoride at room temperature, after 2.5 minutes 32% of the staring material was converted to the desired fluorinated product. In one set of experiments 70% of the fluorinated product was obtained in less than 20 minutes. Two nicotinic acid derivatives were identified as side-products along with the desired product.

Example 2

Reaction of 6-Fluoro-nicotinic acid 2,3,5,6-tetrafluoro-phenyl ester with functionalised RGD peptide Reaction of the fluorinated product of Example 1 (1 mg) with a suitably functionalized RGD peptide (5 mg, prepared as described in WO 01/77415 and WO 03/006491) in a 1:1 solution of acetonitrile sodiumphosphate 0.1 M pH 9 (total 3 mL) gave the desired product as analyzed by LC-MS. LC-MS conditions: Phenomenex Luna C18(2) 3μ 2×50 mm, mobile phase A; Water/0.1% trifluoroacetic acid (TFA) mobile phase B: Acetonitrile/0.1% TFA, flow 0.6 m L/min, 10-30% B over 5 min. Retention time (Rt)=3.42 min, M+H$^+$ (expected 1381.5 found 1381.6)

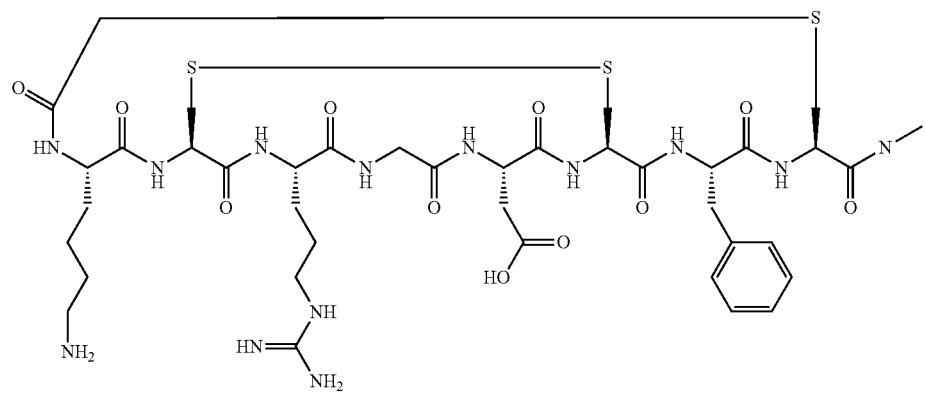

-continued

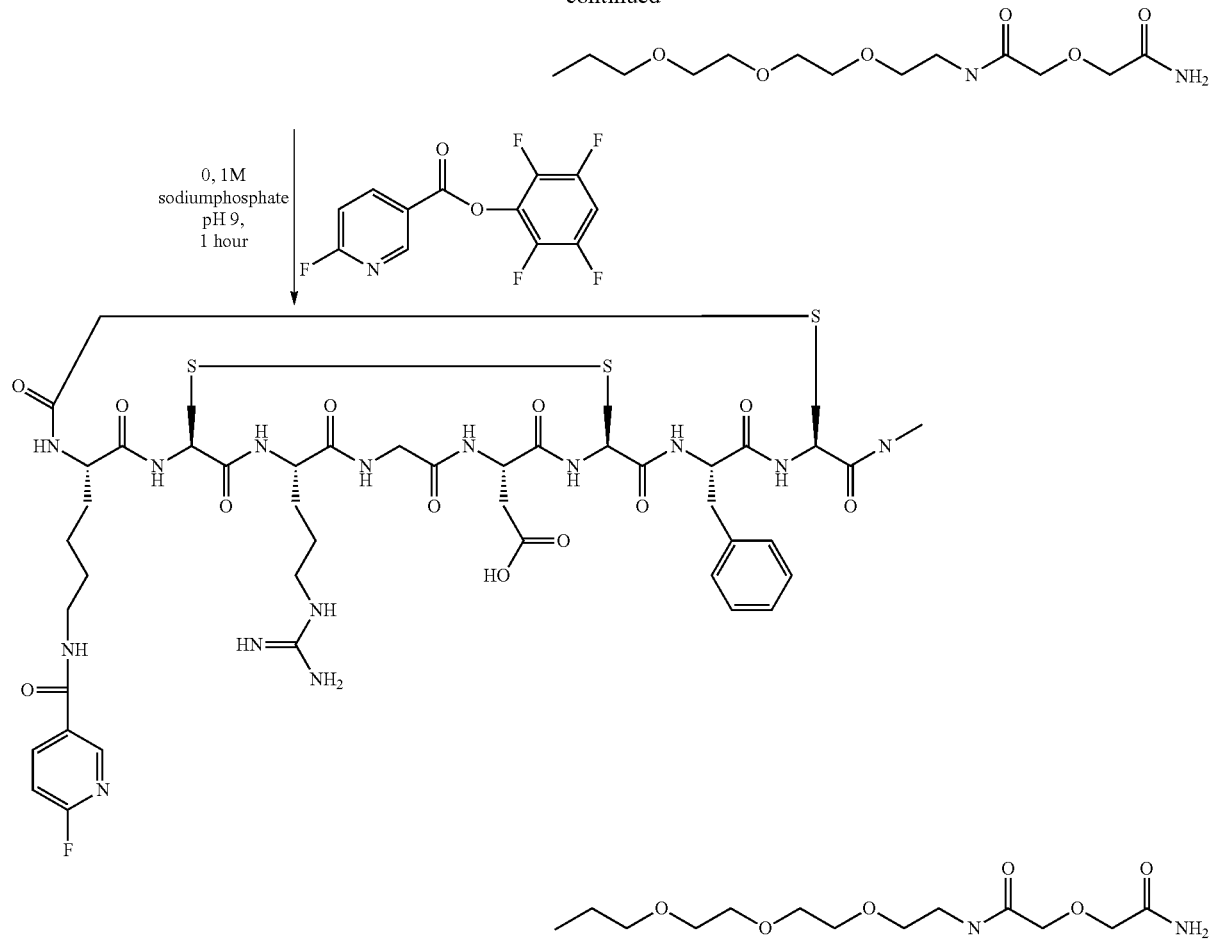

Example 3

Radiosynthesis of 6-[¹⁸F]Fluoro-nicotinic acid 2,3,5,6-tetrafluoro-phenyl ester

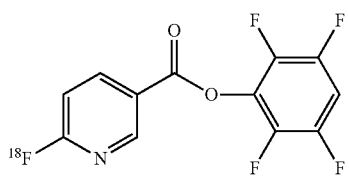 [SMILES: O=C(Oc1c(F)c(F)cc(F)c1F)c1ccc([18F])nc1]

Aqueous [¹⁸F]fluoride (up to 150 MBq) was azeotropically dried in the presence of 15 mg Krytptofix 222 and 3 mg potassium bicarbonate (KHCO₃) heating under N₂ to 100° C. for 9 minutes. During this time 2×1 mL acetonitrile were added and evaporated. After cooling to 40° C., a solution of methanesulfonatetrimethyl-[5-(2,3,5,6-tetrafluoro-phenoxycarbonyl)-pyridin-2-yl]-ammonium (7 mg in 1 mL acetonitrile) was added. The reaction vessel was heated to 40° C. for 10 minutes to effect labelling. The crude reaction mixture was subjected to radio-HPLC (high performance liquid chromatography) and radio-TLC (thin layer chromatography) with co-injection with the cold reference standard to confirm the generation of the target ¹⁸F-compound. Incorporation yields were typically between 50-80% as analyzed by radio-TLC (n=3).

Radio-TLC: Precoated silica gel plates 60 F₂₅₄ (Merck) Gradient n-Hexane/Ethyl acetate 50:50. Instant Imager (Packard BioScience) was used to measure the radioactive distribution on the TLC-plates. Rf: 0.65

Radio-HPLC: Analytical radio-HPLC was performed on an Agilent system (1100 series) with UV detection equipped in series with a γ-detector (Bioscan flow-count). Phenomenex Luna C18(2) column (150×4.6 mm, 5 μm), flow 1.0 mL/min with gradient 20-80% B over 20 min. (UV detection at 214 and 254 nm was combined with a γ-detector). Rt 14.4 min.

Purification

The crude reaction mixture containing -[¹⁸F]Fluoro-nicotinic acid 2,3,5,6-tetrafluoro-phenyl ester in 2 mL acetonitrile, was diluted down to 30% acetonitrile with distilled water. The aqueous solution was passed through a Oasis MCX plus cartridge (conditioned according to the manufacturers recommendations) The cartridge was then rinsed with 5 mL of distilled water. The purified product was then eluted of the column with 100% acetonitrile in a radiochemical purity greater than 90%. All remains of unreacted precursor methanesulfonatetrimethyl-[5-(2,3,5,6-tetrafluoro-phenoxycarbonyl)-pyridin-2-yl]-ammonium remained on the cartridge.

Example 4

Conjugation of 6-[$^{18}$F]Fluoro-nicotinic acid 2,3,5,6-tetrafluoro-phenyl ester to a cyclic RGD-peptide with free amino functionality

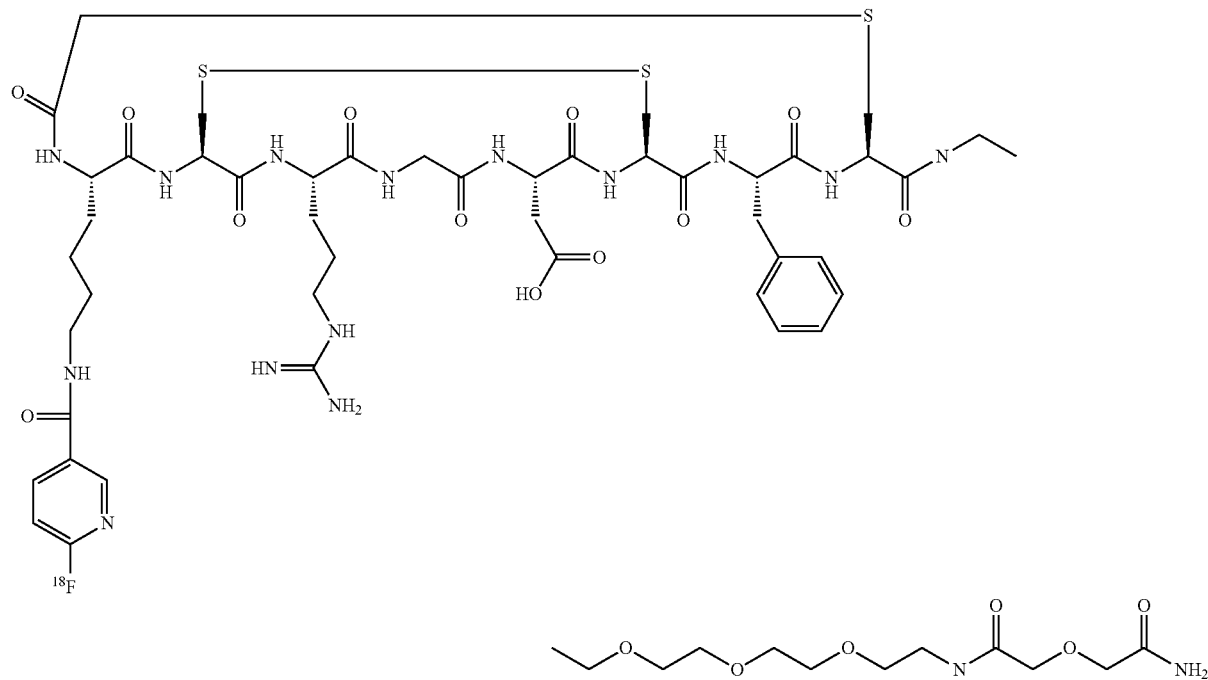

To a solution of the purified 6-[$^{18}$F]Fluoro-nicotinic acid 2,3,5,6-tetrafluoro-phenyl ester in 1.5 mL 1:1 solution acetonitrile/water, was added 3 mg of the suitably functionalized RGD peptide (Mw:1258.47) dissolved in a 1 mL 1:1 solution of acetonitrile and 0.1 M NaHPO$_4$. The resulting mixture with a pH of 9, was heated to 40° C. After 30 minutes a small aliquot of the mixture was analyzed with radio-HPLC. The radiochromatogram showed conversion to the desired product in over 65% yield. The product co-eluted with its $^{19}$F-reference standard.

Radio-HPLC: Analytical radio-HPLC was performed on an Agilent system (1100 series) with UV detection equipped in series with a γ-detector (Bioscan flow-count). Phenomenex Luna C18(2) column (150×4.6 mm, 5 μm), flow 1.0 mL/min with gradient 0-40% B over 20 min. (UV detection at 214 and 254 nm was combined with a γ-detector). Rt 10.0 min.

What is claimed is:

1. A compound of formula (I):

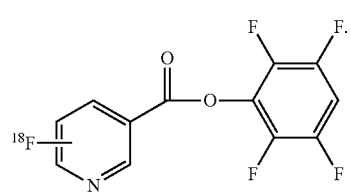

(I)

2. A compound according to claim 1 of formula (Ia):

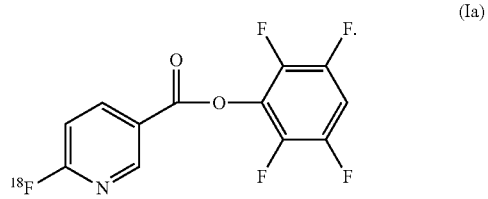 [SMILES: O=C(Oc1c(F)c(F)cc(F)c1F)c1ccc([18F])nc1]

(Ia)

3. A method for $^{18}$F-fluorination comprising reaction of a compound of formula (I) or (Ia) as defined in claim 1 with a compound of formula (III):

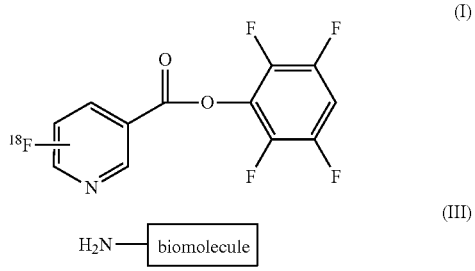

(I)

(III)

to give an $^{18}$F-product of formula (IV):

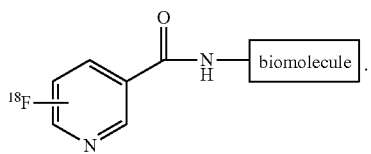

4. A method according to claim 3 wherein the biomolecule is a peptide.

5. A method according to claim 3 wherein the biomolecule is a peptide selected from somatostatin analogues, such as octreotide, bombesin, vasoactive intestinal peptide, chemotactic peptide analogues, a-melanocyte stimulating hormone, neurotensin, Arg-Gly-Asp peptide and its analogues, human pro-insulin connecting peptide, endothelin, angiotensin and formyl-norleucyl-leucyl-phenylalanyl-norleucyl-tyrosyl-lysine.

6. A method according to 3 wherein the biomolecule comprises the fragment:

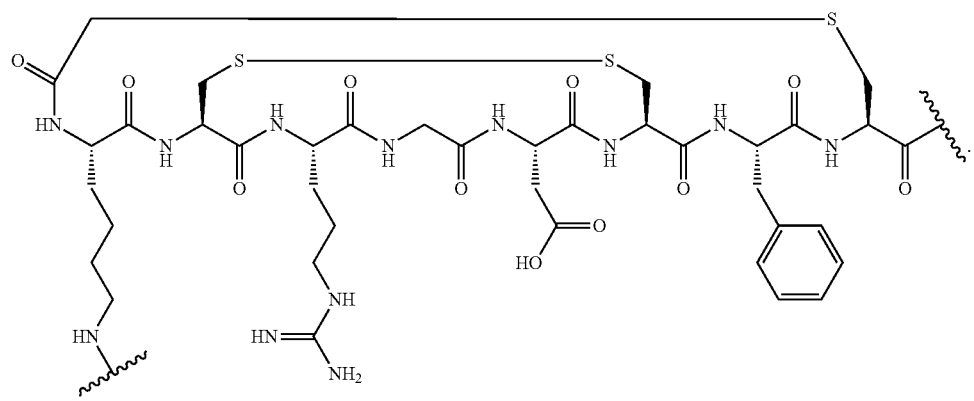 [SMILES: *NCCCC[C@@H]1NC(=O)CSC[C@@H](C(*)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2]

7. A method according to claim 3 wherein the biomolecule is a peptide of formula (A):

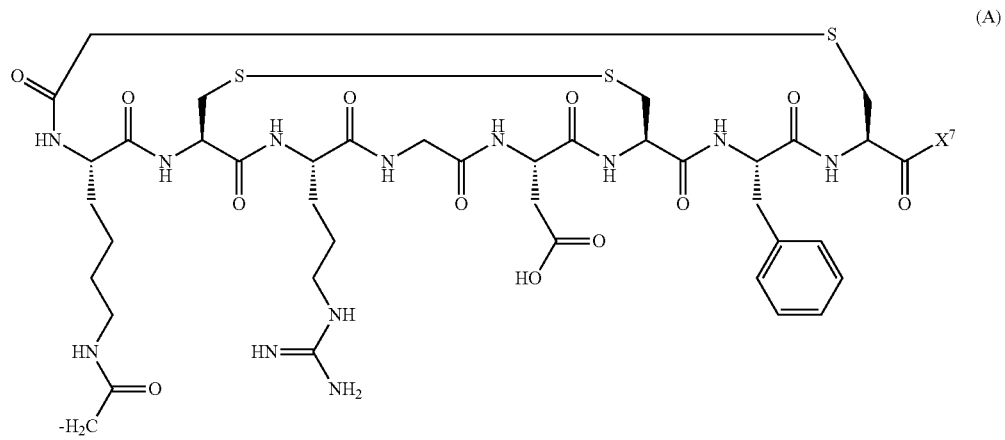

wherein $X^7$ is either —NH$_2$ or

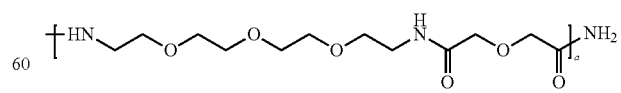

wherein a is an integer of from 1 to 10.

8. A method according to claim 7 wherein a is 1.

* * * * *